United States Patent [19]
Abe et al.

[11] Patent Number: 5,986,171
[45] Date of Patent: Nov. 16, 1999

[54] METHOD FOR EXAMINING NEUROVIRULENCE OF POLIO VIRUS

[75] Inventors: Shinobu Abe; Yoshihiro Ota, both of Saitama; So Hashizume, Chiba; Satoshi Koike, Aichi; Akio Nomoto, Tokyo; Hiromichi Yonekawa, Saitama; Choji Taya, Tokyo; Tatsuji Nomura, Tokyo, all of Japan

[73] Assignees: Japan Poliomyelitis Research Institute, Tokyo, Japan; Central Institute for Experimental Animals, Kanagawa, Japan

[21] Appl. No.: 08/549,701

[22] PCT Filed: Mar. 18, 1994

[86] PCT No.: PCT/JP94/00451

§ 371 Date: Nov. 5, 1995

§ 102(e) Date: Nov. 5, 1995

[87] PCT Pub. No.: WO95/25954

PCT Pub. Date: Sep. 28, 1995

[51] Int. Cl.$^6$ .............................. C12N 5/00; C12N 15/00; C12N 15/09; C12N 15/63
[52] U.S. Cl. ................................... 800/3; 800/18; 800/9; 435/455; 424/9.21
[58] Field of Search ................................ 800/2, 18, 3, 9; 435/172.3, 69.1, 455; 424/9.2, 93.2, 9.21

[56] References Cited

U.S. PATENT DOCUMENTS

| | | | |
|---|---|---|---|
| 5,079,232 | 1/1992 | Ohsawa et al. | 514/25 |
| 5,116,325 | 5/1992 | Paterson | 604/192 |
| 5,573,519 | 11/1996 | Zohmann | 604/272 |

FOREIGN PATENT DOCUMENTS

| | | |
|---|---|---|
| WO 88/08026 | 10/1988 | WIPO . |
| WO 90/10699 | 9/1990 | WIPO . |
| WO 92/07958 | 5/1992 | WIPO . |

OTHER PUBLICATIONS

Wall, Theriogenology, vol. 45, pp. 57–68, 1996.
Strojek & Wagner, Genetic Engineering: Principles and Methods, vol. 10, pp. 221–246, 1988.
Abe et al., Virology, vol. 206, pp. 1075–1083, Feb. 1, 1995.
Horie et al., Journal of Virology, vol. 68, pp. 681–688, Feb. 1994.
Peng et al., 1993, J. Virol. 67:1698–701 (abstract).
Carver et al., 1993, Biotechnol. 11:1263–70 (abstract).
O'Donnell, 1993, Cancer Detect. Prev. 17:307–12 (abstract).
Shi et al., 1993, I Chun Hsueh Pao 20:122–34 (abstract).
Perevozchikov et al., 1993, Mol. Biol. (Mosk) 27:24–37 (abstract).
Shamay et al., 1992, Transgenic Res. 1:124–32 (abstract).
Velander et al., 1992, Proc. Natl. Acad. Sci. USA 89:12003–7 (abstract).
Muller et al., 1992, Gene 121:263–70 (abstract).
Shamay et al., 1992, Mol. Endocrinol. 6:191–7 (abstract).
Shamay et al., 1991, J. Anim. Sci. 69:4552–62 (abstract).
Palmiter et al., 1991, J. Anim. Sci. 69:2995–3004 (abstract).
Wall et al., 1991, Proc. Natl. Acad. Sci USA 88:1696–700 (abstract).
Koval' et al., 1991, Probl. Endokrinol. (Mosk) 37:51–4 (abstract).
Guthrie et al., 1991, Domest. Anim. Endocrinol. 8:423–9 (abstract).
Mullins et al., 1990, Nature 344:541–4 (abstract).
Lemmer et al., 1993, Hypertension 22:97–101 (abstract).
Hammer et al., 1985, "Production of transgenic rabbits, sheep and pigs by microinjection", *Nature* 315:680–683.
Palmiter et al., 1982, "Dramatic growth of mice that develop from eggs microinjected with metallothionein–growth fusion genes", *Nature* 300:611–615.
Tyler & Fields, 1991, "Pathogenesis of viral infections", *Fundamental Virology 2nd Ed.* Fields et al. (eds.), Raven Press, NY, Chap 10, pp. 191–239.
Palmiter et al., 1983, "Metallothionein–Human GH fusion genes stimulate growth of mice", *Science* 222:809–814.

*Primary Examiner*—Brian R. Stanton
*Assistant Examiner*—Jill D. Martin
*Attorney, Agent, or Firm*—Pennie & Edmonds LLP

[57] ABSTRACT

The present invention relates to a method of examining the neurovirulence of a polio virus, which comprises inoculating a polio virus into the spinal cord of a transgenic mouse comprising a gene for a polio virus receptor.

4 Claims, 13 Drawing Sheets

MICROSYRINGE

| | | Tg21 | | | Tg1 |
|---|---|---|---|---|---|
| DOSE | MOUSE NUMBER | NUMBER OF DATES AFTER INOCULATION<br>1 - 3 - 5 - 7 - 9 - 11 - 13 - | DOSE | MOUSE NUMBER | NUMBER OF DATES AFTER INOCULATION<br>1 - 3 - 5 - 7 - 9 - 11 - 13 - |
| $10^2$ TCID$_{50}$ | 1<br>2<br>3<br>4<br>5<br>6<br>7<br>8<br>9<br>10<br>11<br>12<br>13<br>14 | ○○○○○○○○○○○○○○<br>○○○○○○○○○○○○○○<br>○○○○○○○○○○○○○○<br>○○○○○○○○○○○○○○<br>○○○○○○●●●●●●●●<br>○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○ | $10^1$ TCID$_{50}$ | 1<br>2<br>3<br>4<br>5<br>6<br>7<br>8 | ○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○<br>○○○○○○○○○○○○○○ |
| $10^3$ TCID$_{50}$ | 15<br>16<br>17<br>18<br>19<br>20<br>21<br>22<br>23<br>24<br>25<br>26<br>27<br>28 | ○○○○○○○○○○○○○○<br>○○○○○○○○○○○○○○<br>○○○○○○○○○○○○○○<br>○○○○○○●●★<br>○○○○○○●●●●★<br>○○○○○○○○○○○○○○<br>○○○○○○○○○○○○○○<br>○○○○○○○○○○○○○○<br>○○○○○○○○○○○○○○<br>○○○●●●●★<br>○○○○○●●●★<br>○○○○○○○○○○○○○○<br>○○○○○○○○○○○○○○<br>○○○○○○○○○○○○○○ | $10^2$ TCID$_{50}$ | 9<br>10<br>11<br>12<br>13<br>14<br>15<br>16<br>17<br>18 | ○●●★<br>○○○●★<br>○○○●●★<br>○○○○●●●★<br>○●●★<br>○○●●●●★<br>○○○○○○○○○○○○○○<br>○○○○○○●●●●●●★<br>○○○○○○○○○○○○○○<br>○○●●●●●●●●●●●● |
| $10^4$ TCID$_{50}$ | 29<br>30<br>31<br>32<br>33<br>34<br>35<br>36<br>37<br>38<br>39<br>40<br>41<br>42 | ○○○●●●★<br>○●●●●●●●★<br>○○○●●●●●●●●●●<br>○●●●●●●●●★<br>○○○○○○●●●●★<br>○○○○○○●●●●●●●<br>○○○○○○●●●●●●●<br>○○○○○○●●●●●●●<br>○○○○○○●●●●●●●<br>○○○●●●★<br>○○○●●●★<br>○○○●●●★<br>○○○●●●★<br>○○○○○○○○○○○○○○ | $10^3$ TCID$_{50}$ | 19<br>20<br>21<br>22<br>23<br>24<br>25<br>26<br>27 | ○●●★<br>○○○●●●★<br>○●●●●●●★<br>○●●★<br>○●●●●●●●●●●●●●<br>○●●●●●●●●●●●●●<br>○○○○○○●●●●●●●●<br>○●●●●●●●●●●●●●<br>○○○○○○○○○○○○○○ |

METHOD FOR EXAMINING NEUROVIRULENCE OF POLIO VIRUS

This 371 application claims the benefit of PCT/JP94/00451, filed Mar. 18, 1994.

FIELD OF THE INVENTION

The present invention relates to a method of examining the neurovirulence of a polio virus by inoculating a polio virus into the spinal cord of a transgenic, non-primate vertebrate animal with a gene for a polio virus receptor introduced therein.

BACKGROUND OF THE INVENTION

Poliomyelitis is a disease in the human central nervous system caused by a polio virus. The polio virus is divided into 3 serotypes i.e. types 1, 2 and 3, and it is considered that there are a variety of naturally occurring strains having weak (attenuated virus strains) to strong (virulent virus strains) levels of neurovirulence to which the primates only are sensitive.

Natural infection and prevalence of polio have occurred exclusively in the human being since ancient times as an infectious disease. A large number of humans still become infected with polio every year in developing countries. Hence, the eradication of polio in the near future is a task of the human being, and it is expected that a live polio vaccine can be the most effective weapon to solve this problem.

Although an attenuated polio virus has been produced and used as attenuated oral polio vaccine, the attenuated polio viruses may be dangerous for the possible reversion of pathogenicity (paralysis-based neurovirulence) in persons administered or in contact with it. Hence, there is a need for a safe and effective polio vaccine which is free of such pathogenicity. To produce such polio vaccine, consistency tests, particularly tests for neurovirulence of vaccine virus in monkeys, have been indispensable test.

Neurovirulence tests using monkeys, carried out worldwide at present, involve inoculating a predetermined amount of polio virus into the spinal cord of a monkey where the frequency of occurrence of paralysis and the histopathological changes in the central nervous system are clinically observed and numerically expressed in terms of "lesion score". In these prevailing tests for neurovirulence of attenuated polio viruses, a large number of monkeys such as cynomolgus monkeys are used.

However, these neurovirulence tests using monkeys suffer from the following disadvantages: (1) the price of the monkey is too high compared with conventional experimental animals; (2) a person handling the monkey is in the danger of infection with a pathogenic virus from the monkey; (3) the supply of the monkey declines for the protection of wild animals; and (4) wild monkeys are not homogeneous in genetic characteristics, resulting in data fluctuations even with the same sample (scattering results are inevitable).

In spite of these disadvantages, mice and rats cannot be used because such animals other than primates are not sensitive to the polio virus as described above.

SUMMARY OF THE INVENTION

The object of the present invention is to provide a method of examining neurovirulence, which comprises using transgenic non-primate vertebrate animals sensitive to polio virus in simple procedures, thus giving results correlated well with those of the conventional neurovirulence test using monkeys.

As a result of their eager research, the present inventors successfully developed a polio-sensitive test method which gives results correlated well with those of the conventional monkey neurovirulence test by inoculating a polio virus into the spinal cord of a transgenic non-primate vertebrate animal with a gene for a polio virus receptor introduced therein.

That is, the present invention is a method of examining the neurovirulence of a polio vaccine, which comprises inoculating a polio virus into the spinal cord of a transgenic non-primate vertebrate animal with a gene for a polio virus receptor introduced therein. Examples of transgenic non-primate vertebrate animals are transgenic mouse, transgenic rat, transgenic guinea pig and transgenic hamster. Examples of polio vaccines are attenuated strains from type 1, 2 or 3 of polio virus.

DETAILED DESCRIPTION OF THE INVENTION

Figure 1:
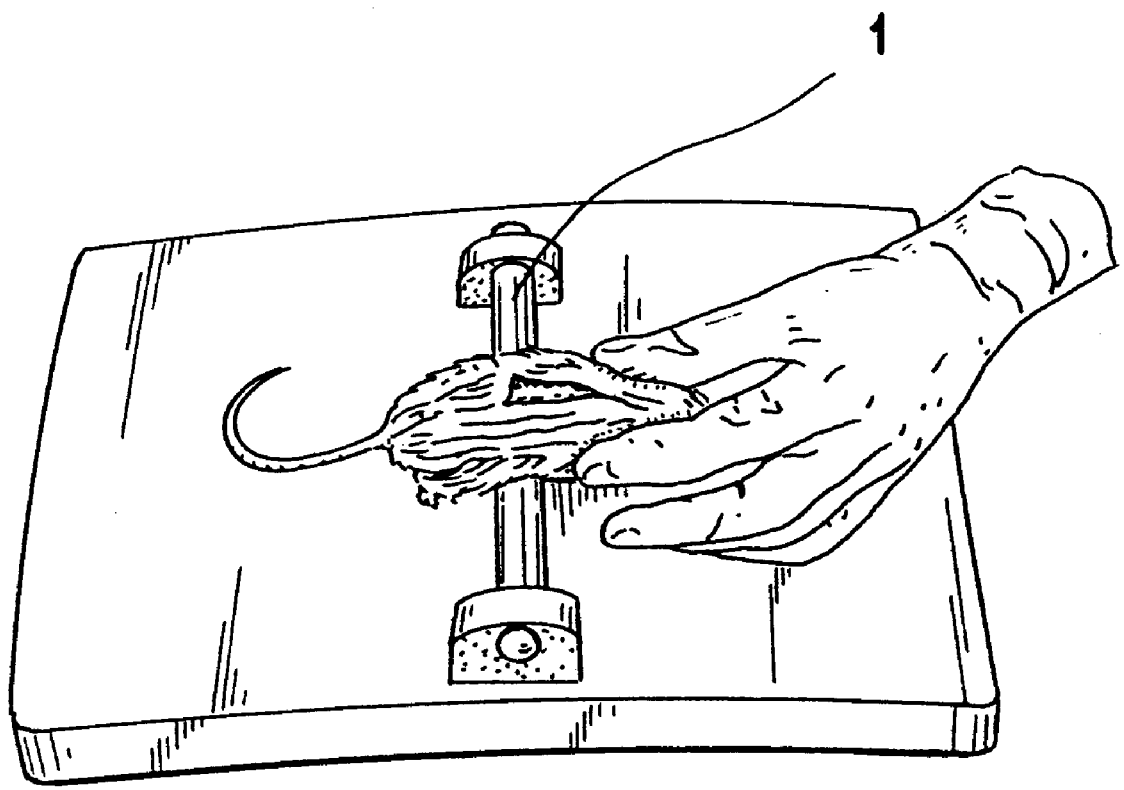
Figure 2:
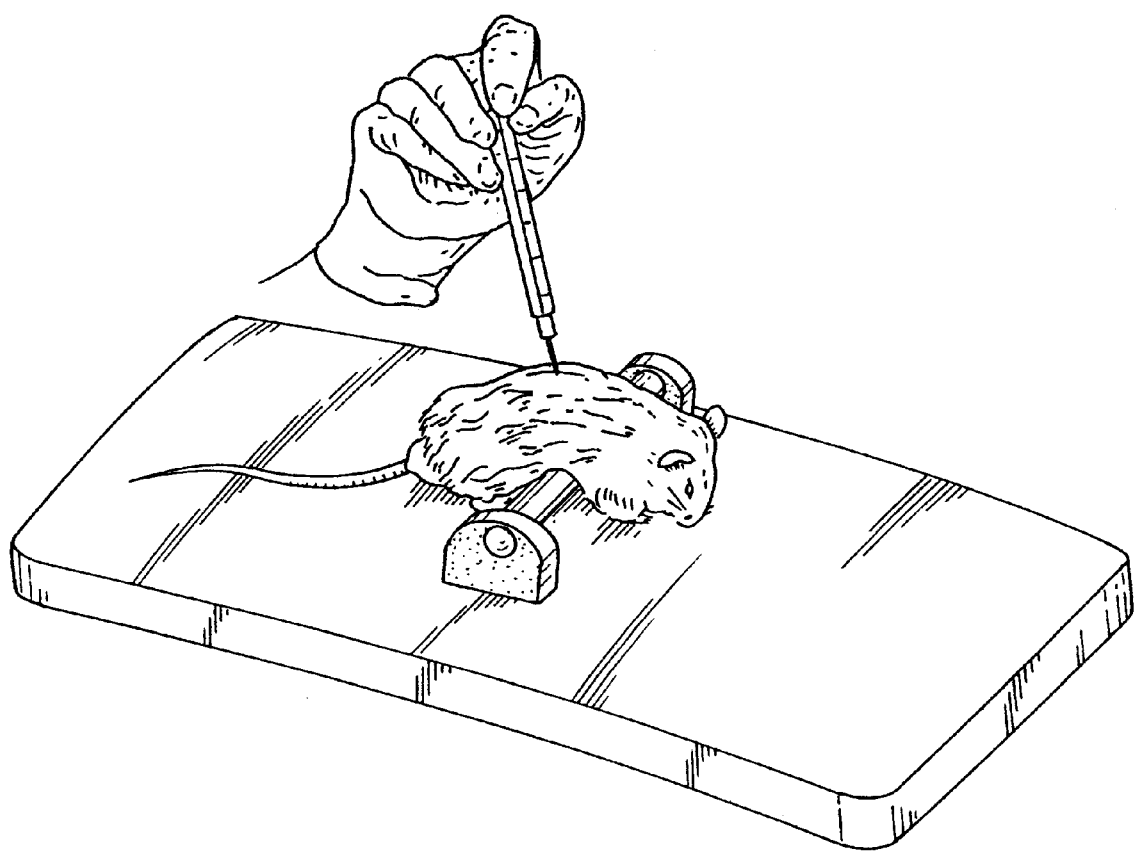
Figure 3:
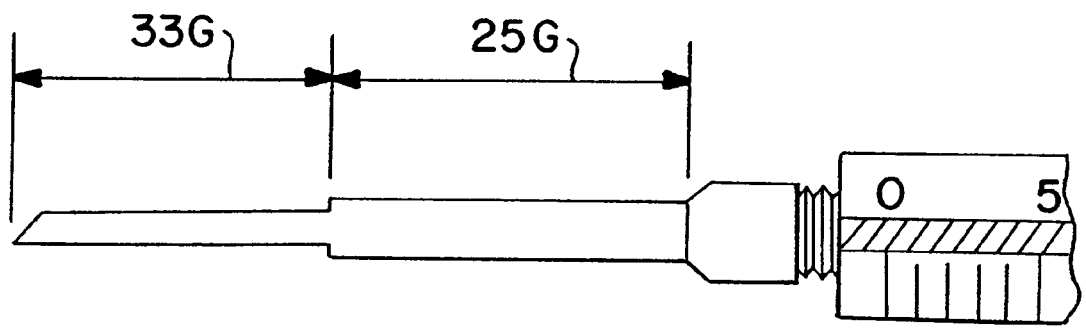

Hereinafter, the present invention is described in detail.

The transgenic non-primate vertebrate animals (referred to hereinafter as "transgenic animals") are as described below.

The transgenic mice, developed by Ruibao Ren et al. (Ren, R., et al., Cell., 63, 353–362, 1990) and Koike et al. (Koike, S., et al., Proc. Nat'l. Acad. Sci. USA., 88, 951–955, 1991), are transgenic, polio virus-sensitive mice (referred to hereinafter as "TgPVR") carrying a gene for a polio virus receptor (referred to hereinafter as "PVR") on human HeLa cells introduced into the mouse gene. The TgPVR used in the present invention may be any strain of mouse including ICR strain, C57BL/10 strain, IQI strain, etc., which are preferably 4- to 6-week-old. For example, the ICR strain may be a 4- to 6-week-old transgenic mouse that is a homozygote or heterozygote named ICR-TgPVR21 or a transgenic mouse that is a heterozygote named ICR-TgPVR1 [available from "Jikken Doubutsu Chuo Kenkyusho" (Central Institute for Experimental Animals, Foundation)]. The mice can be used regardless of sex.

The transgenic rats, transgenic hamsters and transgenic guinea pigs can also be obtained in the same manner as that of the polio virus-sensitive transgenic mice by inserting a trace amount of cloned human PVR DNA into female or male pronuclei of fertilized eggs, then returning them to the oviducts of pseudo-pregnant animals, and screening born and grown animals for those carrying the human PVR gene.

The transgenic rats, transgenic hamsters and transgenic guinea pigs may be derived from any strain. For example, the transgenic rats may be derived from W (Wister) strain, Spraque-Dawky strain, F344 strain, etc.; the transgenic hamsters from Syrian hamster NSJ strain etc.; and the transgenic guinea pigs from Hartley strain etc.

The virus used in the present invention is any of types 1, 2 and 3 of polio virus. Preferable examples are 7 kinds of virus (F113, S1A, S1B, S1C, S1D, S1D-38/2 and S1D-38/4) having different levels of neurovirulence and derived from type 1 of Sabin (type 1 of polio virus) as attenuated vaccines (Sabin, A. B., J.A.M.A., 194, 130–134, 1965), and their properties will be described below.

F113, a reference virus of type 1 of attenuated poliovirus available from National Institute of Health, Japan, is a standard virus in Japan for examining the neurovirulence of type 1 of live polio vaccine. S1A, S1C and S1D are viruses with suitable neurovirulence as vaccines. S1B is a virus with extreme attenuation selected by plaque cloning method from type 1 of Sabin strain. S1D-38/2 and S1D-38/4 are viruses obtained by subculturing S1D for 2- and 4-passages respectively at 38° C. in renal cells from green monkeys for the neurovirulence has increased to an intolerable level as vaccine.

The amount of virus inoculated according to the present invention is indicated in terms of "$TCID_{50}$ (tissue culture infective dose)" which generally means the amount of a sample containing infectious virus which causes infection of 50% of cultured cells upon inoculation.

In the present invention, 1 $TCID_{50}$ means the amount of virus which upon inoculation causes infection (cytopathogenic effect, referred to hereinafter as "CPE") of 50% of cultured GMK2 cells, i.e. a renal cell line derived from green monkeys and established by National Institute of Health, Japan. Hence, $10^4$ $TCID_{50}$ means $10^4$ times that amount of virus which causes CPE in 50% of GMK2 cells or similar cultured cells in culture tubes.

This infective dose expressed in "$TCID_{50}$" can be determined in a roller tube method using GMK2 cells as illustrated below in the examples.

The inoculation of the virus into the transgenic animal is carried out in the following manner. The animal is anesthetized with pentobarbital, ether, or the like. The anesthetized transgenic animal is disinfected on the back with ethanol and then cut along the midline to expose the spine. A needle can be easily inserted intervertebrally into the transgenic animal by cutting skin with the abdomen being placed on a stand as shown in FIG. 1.

Then, the needle is inserted into the lumbar cord, aiming at its enlargement, as shown in FIG. 2. Whether or not the needle has been inserted correctly into the lumbar cord can be confirmed by observing the occurrence of jerk in the hind limb.

The reason the needle is inserted into the enlargement of the lumbar cord is that because the lumbar cord is an organ (which in the monkey is the most sensitive to polio virus) containing the highest level of mRNA of PVR and a high level of PVR, this organ is expected highly sensitive and desirable for measuring the neurovirulence of the polio virus including virulent or attenuated strains.

The inoculation volume is preferably in the range of 5 to 20 $\mu$l to ensure inoculation with less mechanical damage to the spinal cord of the transgenic animal. For a mouse, the inoculation volume is usually 5 $\mu$l.

The needle is preferably a 2-step needle as shown in FIG. 3. The part of the needle to be inserted is 33-gauge piercing tip (0.2 mm diameter) and 7 mm long to prevent it from passing through the lumbar cord upon insertion.

The syringe may be of any type, but a 25-$\mu$l microsyringe is preferable to inject the above range of volume.

After the virus was inoculated in the manner described above, the skin of the back is closed with a commercial quick-drying glue.

The animals thus inoculated are then clinically observed for a predetermined period of time usually over a period of 14 days, and animals with paralysis within 24 hours after inoculation are excluded as those mechanically damaged by inoculation from the subject to be evaluated. Neurovirulence is determined by quantification of clinical phenomena in terms of $PD_{50}$ or $LD_{50}$ or latent period of clinical symptoms or by pathological examination of the central nervous system including the spinal cord and brain.

The term "$PD_{50}$" means that amount of virus which causes paralysis of 50% of transgenic animals upon inoculation, and the term "$LD_{50}$" means that amount of virus which causes death of 50% of transgenic animals. Both of them are clinically used to indicate viral neurovirulence. Both can be calculated according to the Reed-Muench method (Reed, L. J., et al., Am. J. Hyg. 27, 493–497, 1938) or the Spearman-Karber method (Lab. Tech. in Rabies, 3rd Ed., Kaplan, M. M. and Koprowski, H., WHO, 1973).

Clinical observation is made of the occurrence, degree and progress of paralysis in the four limbs as well as the change of animal weight. To prepare a sample for pathological examination, the animal body itself or the brain and spinal cord are fixed in 10% formalin, then embedded in paraffin, cut into thin sections of 6 to 9 $\mu$m in thickness and stained with gallocyanine. The sections are examined under an optical microscope on infiltration of lymphocyte, mononuclear cell, etc., denaturation and disappearance of nerve cell, for evaluation of neurovirulence. The pathological changes in the tissues can be determined according to WHO (World Health Organization) using a method for evaluating the neurovirulence of polio vaccine in monkeys (WHO Tech. Rep. Ser., 800, 30–86, 1990). In this method, the average score in each animal of the pathological changes in the central nervous system including the spinal cord (lumbar cord, cervical cord) and the brain (midbrain, pons, medulla oblongata, cerebrum and others) is determined, and then the average score of those changes in a group of animals is determined as lesion score (referred to hereinafter as "LS").

BRIEF DESCRIPTION OF THE DRAWINGS

FIG. 1 shows incision of the back of a mouse (1: a stand).

FIG. 2 shows inoculation into the spinal cord of a mouse.

FIG. 3 shows a micro syringe and a needle.

FIG. 4 shows the result of clinical examination of mice inoculated with virus.

FIG. 5*a* shows the result of pathological examination of tissues (slightly magnified) from the lumbar cord of No. 39 mouse (Tg21) shown in FIG. 4.

FIG. 5*b* is high magnification of FIG. 5*a*.

FIG. 5*c* shows the result of pathological examination of tissues (slightly magnified) from the cervical cord of No. 24 mouse (Tg21) shown in FIG. 4.

FIG. 5*d* is high magnification of FIG. 5*c*.

FIG. 5*e* shows the result of pathological examination of tissues from the brain particularly olivary nuclei of the medulla oblongata of No. 24 mouse (Tg21) shown in FIG. 4.

FIG. 5*f* shows the result of pathological examination of tissues from the brain particularly olivary nuclei of the medulla oblongata of No. 24 mouse (Tg21) shown in FIG. 4.

FIG. 5*g* shows the result of pathological examination of tissues (slightly magnified) from the lumbar cord of a monkey.

FIG. 6 shows a correlation between neurovirulence test results using monkeys and those using TgPVR.

FIG. 7 shows the quantity of virus in the brain and the spinal cord in TgPVR after inoculation intraspinally.

EXAMPLES

The present invention is described in more detail by reference to the following examples, which however are not intended to limit the scope of the invention.

Example 1.

Neurovirulence Test Using TgPVR (1) TgPVR

The TgPVR animals used were ICR-TgPVR21 (homozygote or heterozygote, referred to hereinafter as "Tg21") and ICR-TgPVR1 (heterozygote, referred to hereinafter as "Tg1") which both are supplied by "Jikken Doubutsu Chuo Kenkyusho" (Central Institute for Experimental Animals, Foundation). Both are 6-week-old mice derived from polio virus-sensitive ICR mice carrying a human gene for HeLa cell PVR. For each of viral dilutions, 5 to 20 TgPVR animals were used.

(2) Viral Preparation

Before inoculation, each viral sample was examined for infective titer ($TCID_{50}$) using GMK 2 cells in the following roller tube method.

An 0.2 ml each of 10-fold serial dilutions of viral material was inoculated into 5 or more roller tubes containing cultured GMK2 cells. After inoculation, the tubes were incubated for 7 days at 36° C. CPE in the tubes was examined for determination of $TCID_{50}$.

Seven attenuated viruses (F113, S1A, S1B, S1C, S1D, S1D-38/2 and S1D-38/4, available from "Nippon Polio Kenkyusho" (Japan Poliomyelitis Research Institute)) with different levels of neurovirulence derived from type 1 of Sabin strain were subjected respectively to 10-fold serial dilutions with medium (Medium 199) containing 0.225% sodium bicarbonate to prepare samples containing $10^1$ to $10^5$ $TCID_{50}/5\ \mu l$.

(3) Inoculation Into the Spinal Cord of TgPVR

TgPVR was anesthetized by injecting 0.3 ml of 5 mg/ml pentobarbital into the abdomen. Ether inhalation was additionally carried out where further anesthesia was required.

Hair on the back of anesthetized TgPVR was sterilized with ethanol and then cut about 2 cm along the midline to expose the spine.

Before inoculation of the virus, the stand illustrated in FIG. 1 was placed under the abdomen, and the back was further opened intervertebrally in a thoracicolumbar portion in the curved spine. A needle was inserted into the lumbar cord, aiming at its enlargement (FIG. 2). Upon insertion of the needle into the lumbar cord, TgPVR showed jerk in the both or a hind limb. After the occurrence of the jerk was confirmed, TgPVR (5 to 20 animals per group) was inoculated with 5 $\mu l$ each of the serial viral dilutions prepared in (2) above. These dilutions contained that dose of polio virus which permits the onset of the disease in 10% or less to 90% or more of TgPVR animals.

The needle used was a 2-step needle as shown in FIG. 3 where the part of the needle to be inserted is 33 G in thickness (0.2 mm diameter and 7 mm length) and the syringe is a $^{25}$-$\mu l$ microsyringe.

After inoculation, the skin of the back was closed with a quick-drying glue sold under the trade name Alon-alpha and made by Toagosei Chemical Industry Co., Ltd., Japan.

TgPVR with abnormal phenomena (e.g. paralysis in the hind limb) within 24 hours after inoculation were excluded from the subject to be examined.

(4) Neurovirulence Test Using TgPVR (i) Clinical Observation

Each TgPVR inoculated as described in (3) above was maintained in a individual cage and observed clinically for 14 days.

The results are shown in FIG. 4 where "○" indicates normal mouse, "●" paralysis, and "★" dying or dead.

After inoculation into the spinal cord with enough amount of virus to make paralysis, TgPVR showed flaccid paralysis on one or both sides in the hind limbs, which paralysis proceeded rarely to the fore limbs. In most cases, a paralysis occurred on 2nd to 7th days after inoculation. After the onset of paralysis, some survived over 14 days while some died, and this depend on the dose of inoculated virus and virulence. Care was taken of the position of the feeder because the mouse with a paralysis could not drink water from the feeder in a high position.

$PD_{50}$ and $LD_{50}$, based on theses clinical observations, were calculated respectively according to the Reed-Muench method (Reed, L. J., et al., Am. J. Hyg. 27, 493–497, 1938).

In case F113 was used as virus, the results were $10^{3.3}$ $TCID_{50}$ ($PD_{50}$) and $10^{3.6}$ $TCID_{50}$ ($LD_{50}$) with respect to Tg21, and $10^{1.6}$ $TCID_{50}$ ($PD_{50}$) and $10^{2.2}$ $TCID_{50}$ ($LD_{50}$) with respect to Tg1.

The results indicate that the clinical phenomena in Tg21 and Tg1 are clearly dose-dependent and that both Tg21 and Tg1 can be used in an assay system. However, the Tg1 animals were found to be too highly sensitive because 50% or more of them showed a paralysis in a viral dose of $10^2$ $TCID_{50}$. Tg21 possessed more appropriate range of sensitivity.

Tg21 was clinically examined 3 times, and the reproducibility of the test was confirmed. In each experiment, 4 to 5 TgPVR animals were used for each predetermined viral concentration. The $PD_{50}$ values obtained in the respective experiments were very close to one another ranging from $10^{3.25}$ to $10^{3.33}$ $TCID_{50}$, indicating that this experiment system was highly reproducible. Furthermore, a good correlation between paralysis occurrence and pathological change was indicated in this experiment system using TgPVR as described below. Hence, clinical phenomena in both $PD_{50}$ and $LD_{50}$ can be satisfactory indicators of neurovirulence.

(ii) Pathological Examination of Central Nervous System

For pathological examination of central nervous system from TgPVR, the brain and spinal cord of TgPVR that died or moribund (the moribund mouse is shown to be dead in Table 1) over the period of clinical observation were fixed in 10% formalin on that day.

Samples of the brain, such as cortex, midbrain, thalamus, pons, cerebellum and medulla oblongata and samples of the spinal cord, such as 3 to 6 sections of cervical cord, thoracic cord and lumbar cord were embedded in paraffin in a usual manner and cut into thin sections in 6 to 9 $\mu m$ thickness as samples for histopathological examination. Each section was stained with gallocyanine and examined under a microscope. The lesion score of each tissue was determined according to the WHO method of evaluating the neurovirulence of polio vaccine using monkeys.

The results of pathological changes in the central nervous shown in Table 1.

TABLE 1

| | | | histopathological observation | | | |
|---|---|---|---|---|---|---|
| number of | mouse | clinical | brain | spinal cord | | |
| viruses | number | observation | 1 2 3 4 5 6 | CC | TC | LC |
| $10^2$ $TCID_{50}$ | 10 | P(−) | 0 0 0 0 0 0 | 0 | 0 | 0 |
| | 11 | P(−) | 0 0 0 0 0 0 | 0 | 0 | 0 |
| | 12 | P(−) | 0 0 0 0 0 0 | 0 | 0 | 0 |
| | 13 | P(−) | 0 0 0 0 0 0 | 0 | 0 | 0 |
| | 14 | P(−) | 0 0 0 0 0 0 | 0 | 0 | 0 |

TABLE 1-continued

| number of viruses | mouse number | clinical observation | brain 1 2 3 4 5 6 | spinal cord CC TC LC |
|---|---|---|---|---|
| $10^3$ TCID$_{50}$ | 24 | P(+) 4-9(S) | 1 0 0 1 2 2 | 2 2 2 |
| | 25 | P(+) 6-9(S) | 1 0 1 2 1 1 | 2 4 3 |
| | 26 | P(−) | 0 0 0 0 0 0 | 0 0 0 |
| | 27 | P(−) | 0 0 0 0 0 0 | 0 0 0 |
| | 28 | P(−) | 0 0 0 0 0 0 | 0 0 0 |
| $10^4$ TCID$_{50}$ | 38 | P(+) 4-7(S) | − 0 0 1 1 − | 2 3 3 |
| | 39 | P(+) 4-7(S) | 1 0 0 1 2 1 | 3 3 4 |
| | 40 | P(+) 4-7(S) | − 0 − − 1 1 | 3 2 2 |
| | 41 | P(+) 4-7(S) | 1 0 0 1 1 2 | 3 2 3 |
| | 42 | P(−) | 0 0 0 0 0 0 | 0 0 0 |

In the item "mouse number" in Table 1, each number corresponds to the mouse number of Tg21 in FIG. 4 as described in (i) above. In the item "clinical observation", the symbol "P(−)" means that no paralysis was observed for 14 days, while "P(+)" means that a paralysis was observed. For example, "P(+) 4-9(S)" means that the animal showed a paralysis on 4th day and died on 9th day after inoculation.

In the item "histopathological observation", the symbols mean as follows: 1, the cortex; 2, the thalamus; 3, the midbrain; 4, the cerebellum; 5, the pons; 6, the medulla oblongata; CC, the cervical cord; TC, the thoracic cord; and LC, the lumbar cord. The symbol "−" means that no observation was made of that organ.

Figure 5A:
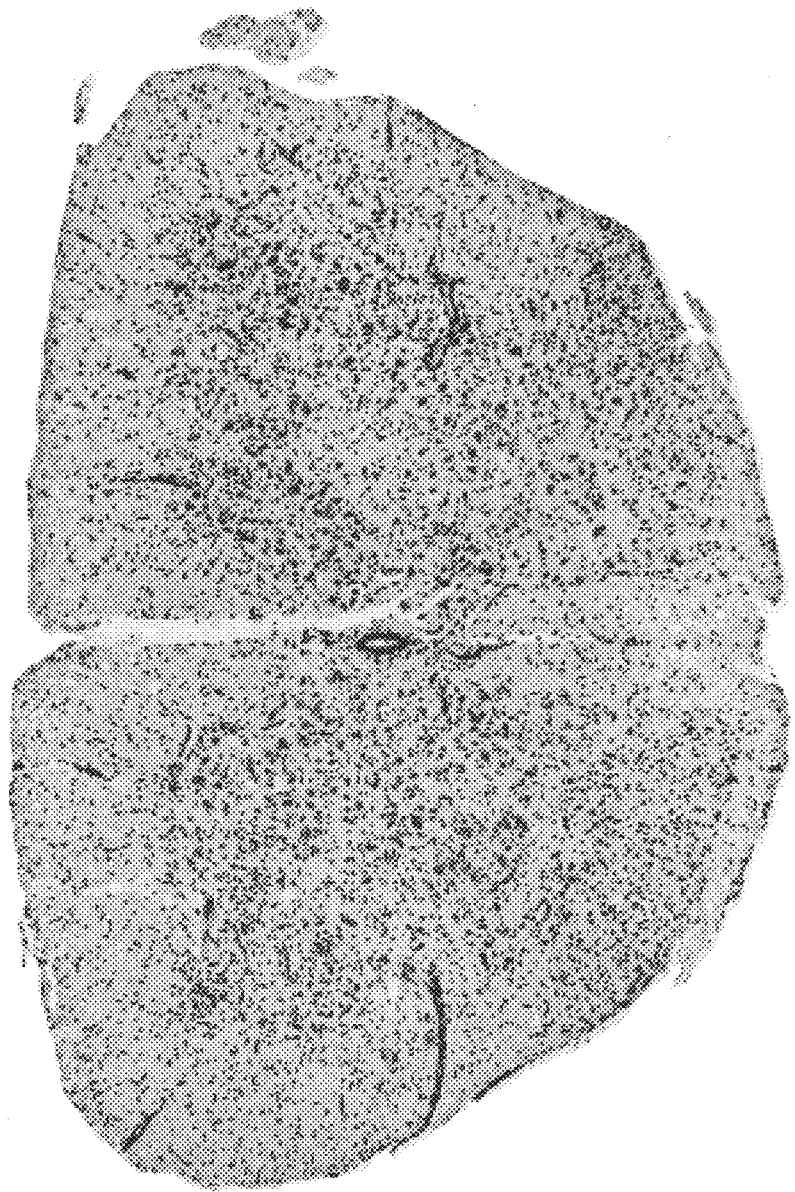
Figure 5B:
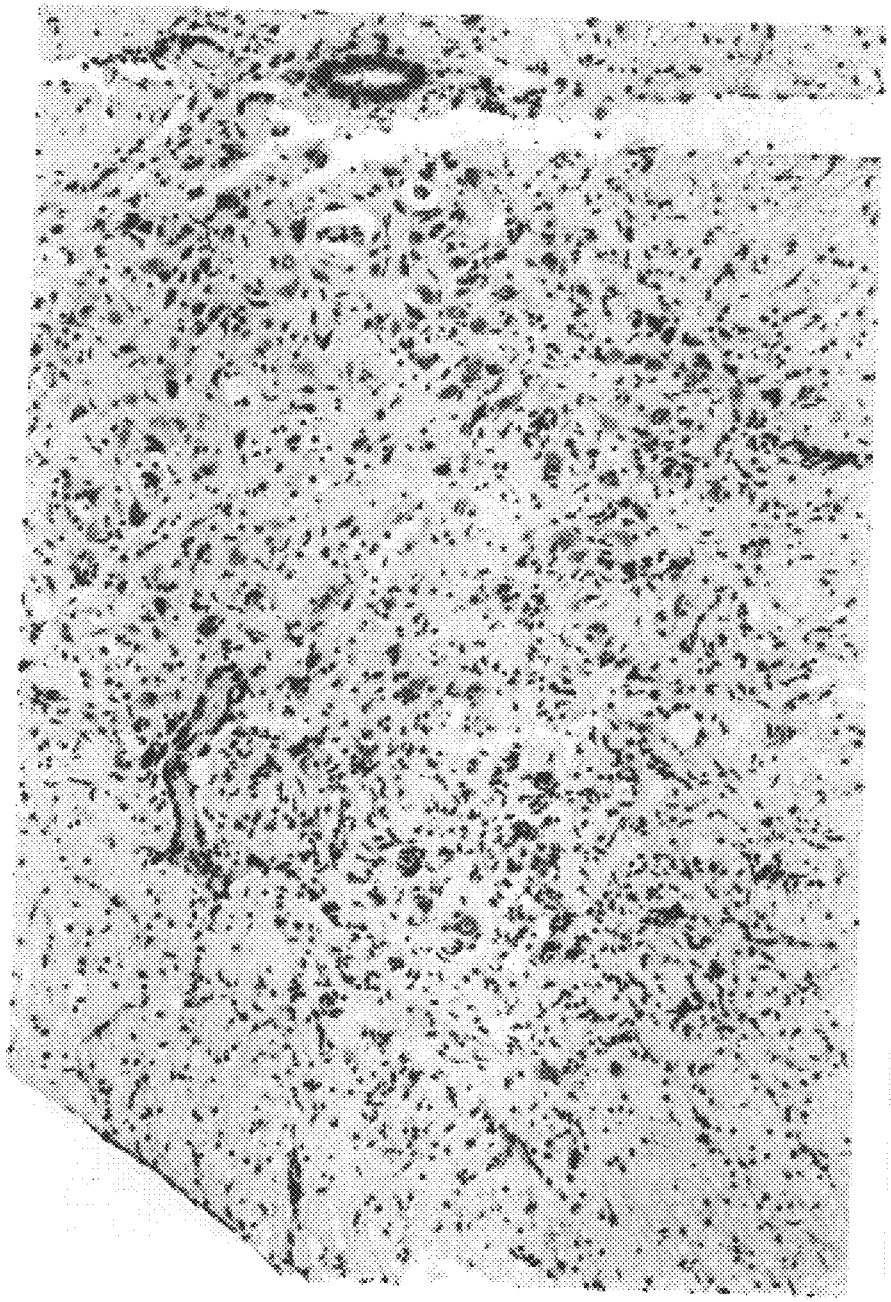
Figure 5C:
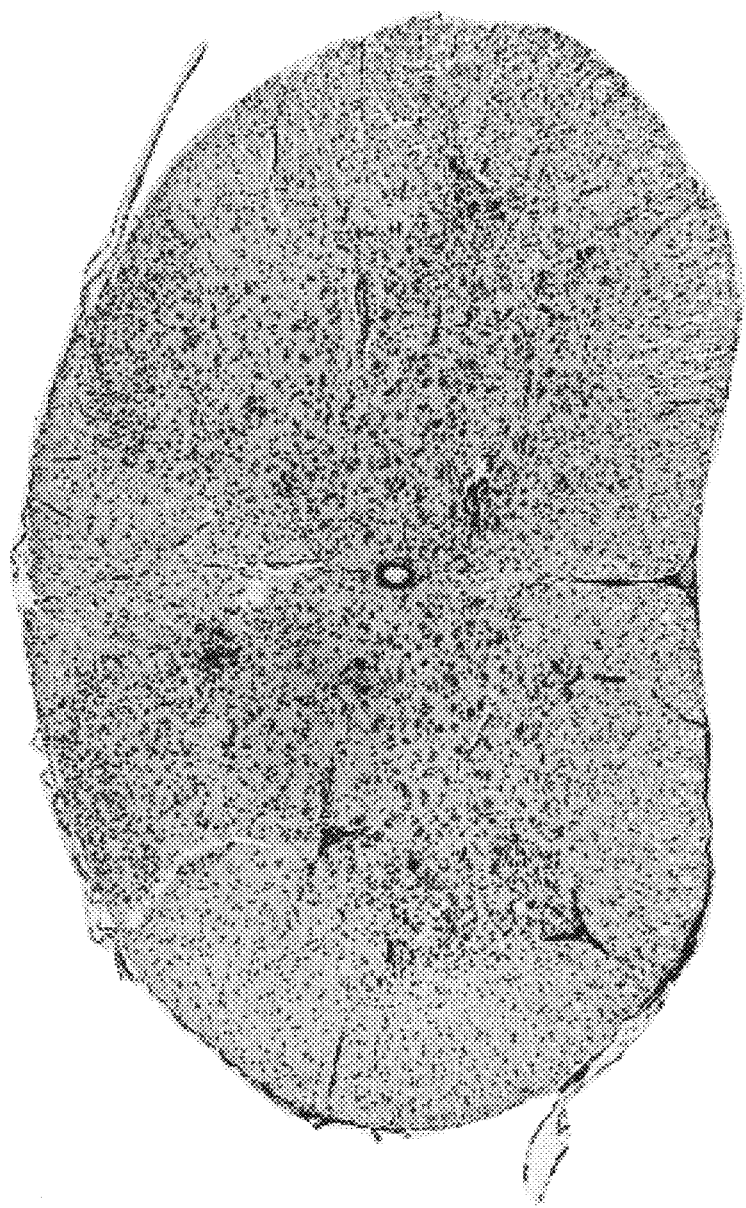
Figure 5D:
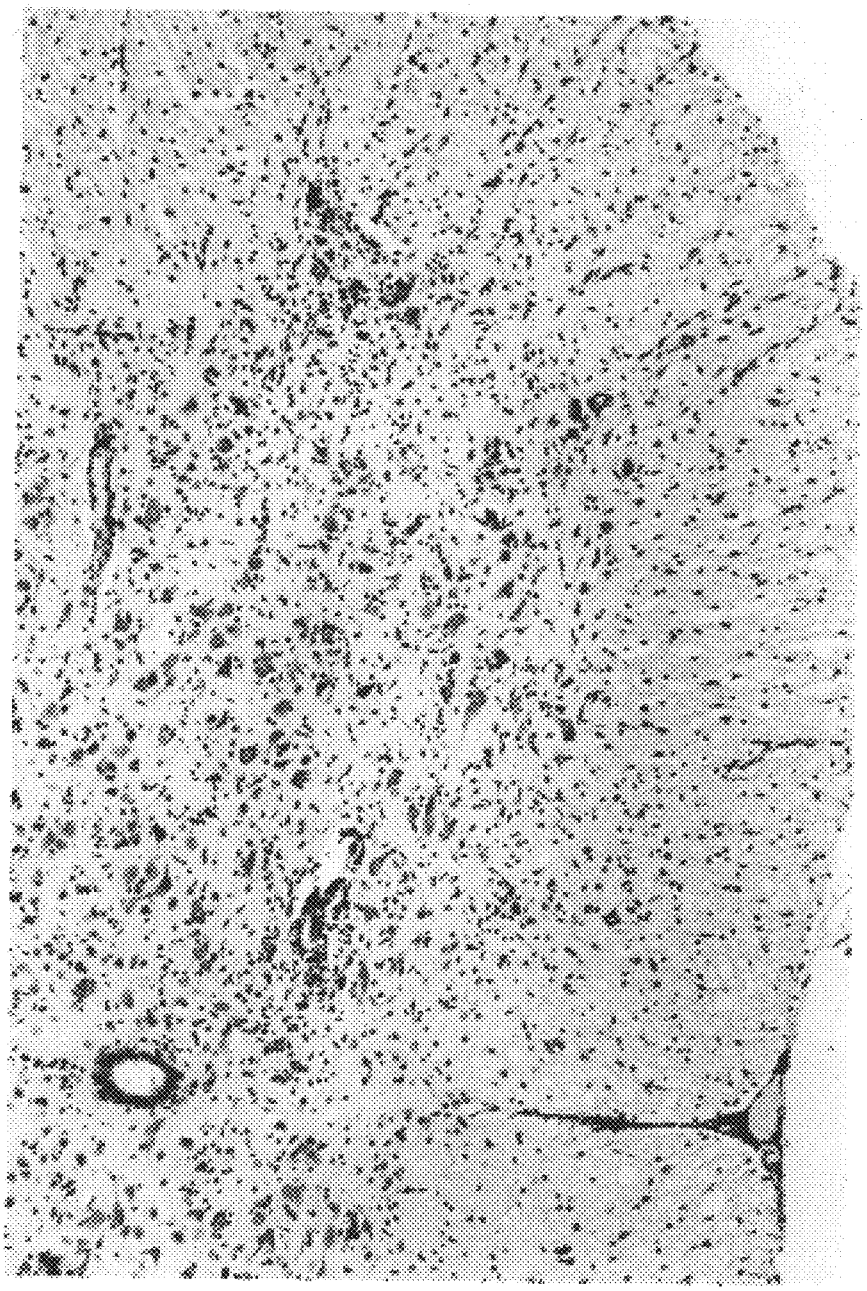
Figure 5E:
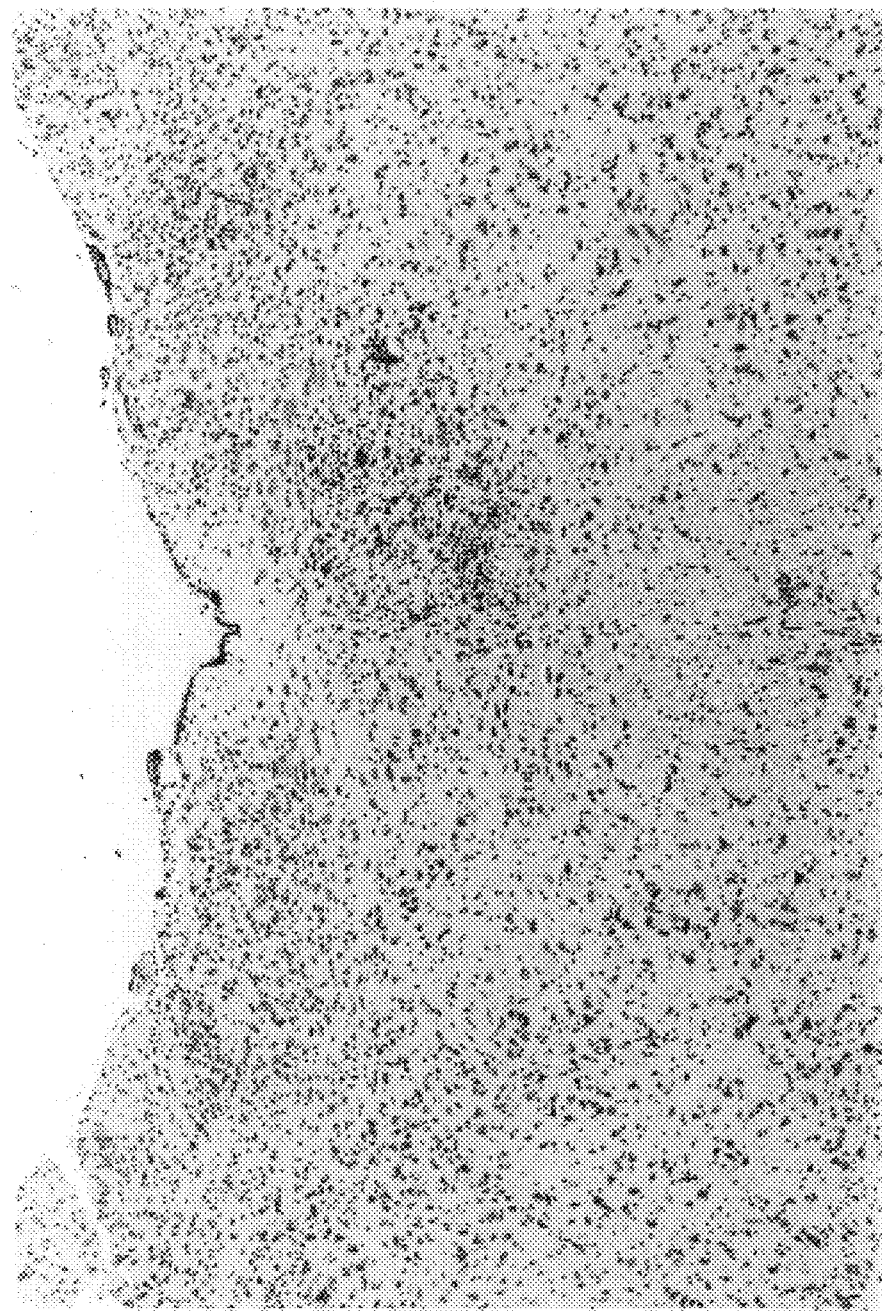
Figure 5F:
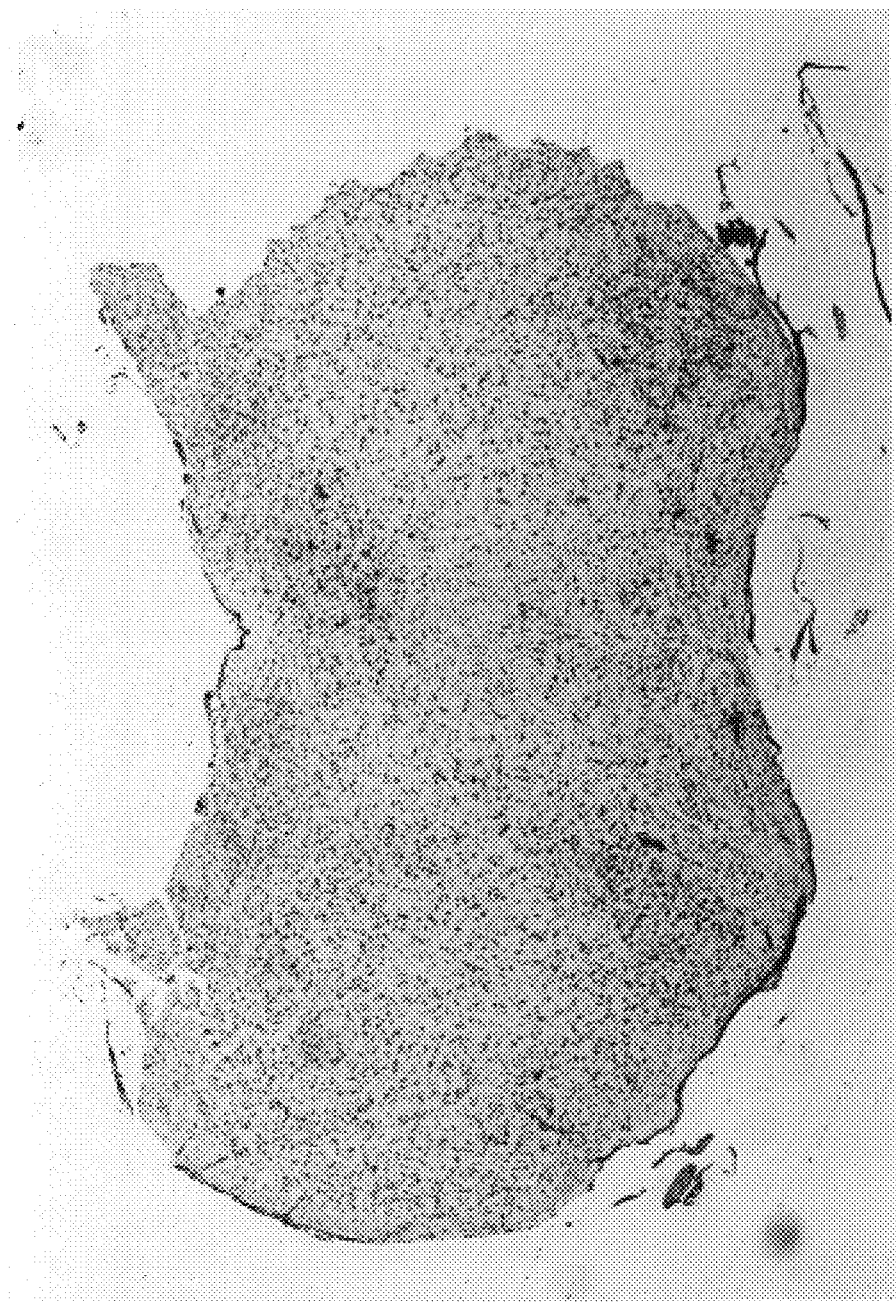
Figure 5G:
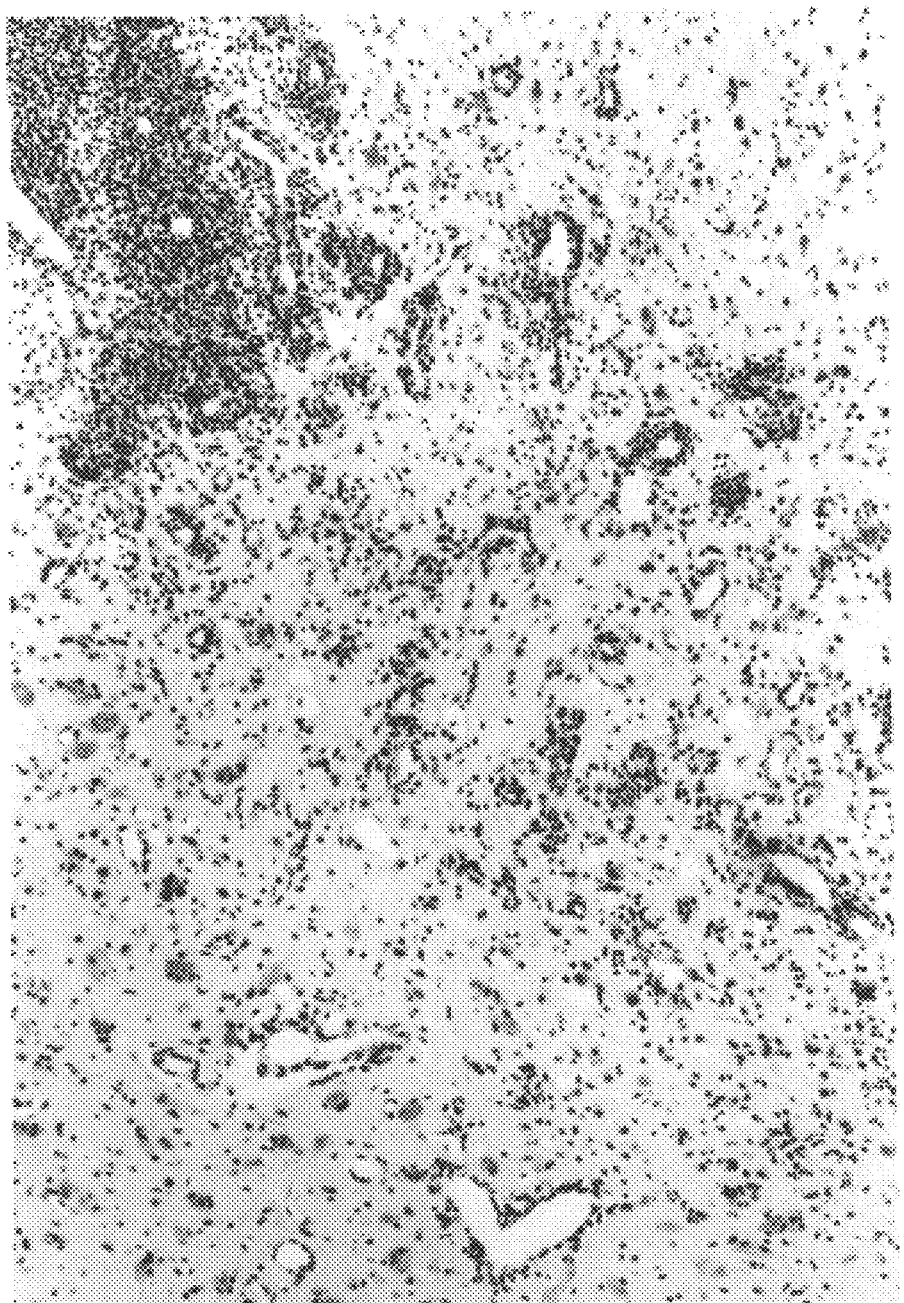

As is evident from Table 1, the lumbar cord showed the highest lesion score. Further, the lesion scores in the lumbar cord agreed well with the occurrence of paralysis. These lesion scores in the lumbar cord are based on the denaturation and disappearance of motoric nerve cells in the gray matter of ventral horn. A less degree of infiltration of mononuclear cells including microglia, lymphocyte, etc., was further observed as inflammation reaction (FIGS. 5a and 5b). In the TgPVR animals with lesions in the lumbar cord, light but prevailing similar lesions were observed in the cervical cord as well as in the thoracic cord (FIGS. 5c and 5d). Further lesions were also observed in the brain, particularly in the medulla oblongata and pons (FIGS. 5e and 5f).

As described above, the lesions in the lumbar cord spread over through the thoracic cord and cervical cord to the medulla oblongata and pons in almost all cases (Table 1). This result indicates that the virus can readily transfer in the central nervous system of Tg21, and TgPVR animals can thus be used as substitutes for monkeys to examine the neurovirulence of polio virus.

Lesions similar to those of monkey (FIG. 5g) were observed in the central nervous system of TgPVR inoculated in the spinal cord. The favorable sites of occurrence of these lesions resembled those of monkeys, but the infiltration of mononucleus cells including microglia or lymphocyte were not so striking as in monkeys (FIGS. 5a to 5g). These pathological phenomena were observed not only in TgPVR which died soon after paralysis, but also in TgPVR with paralysis over a long period of time. In the case of TgPVR which died soon after paralysis, the main pathological phenomena were the denaturation and disappearance of nerve cells.

Example 2.

Sensitivity of TgPVR Inoculated in the Spinal Cord

F113, a reference virus as type 1 of Sabin strain in the neurovirulence test in Japan, was inoculated into the brain of Tg1 out of 4 TgPVR strains (Tg1, Tg5, Tg8 and Tg21) established by Koike et al. A dosage of $10^6$ TCID$_{50}$ did not cause any paralysis in Tg1, while $10^{6.5}$ TCID$_{50}$ caused a paralysis. Because this dosage is too high, it appears that the inoculation of F113 virus into the brain of Tg1 is not suitable for the conventional method of examining the neurovirulence of vaccine.

On the other hand, the inoculation of F113 virus into the spinal cord of Tg1 caused a paralysis in 8 out of 10 animals (80.0%) even in a dosage of $10^2$ TCID$_{50}$.

As the control, ICR mice (i.e non-transgenic mice) did not show any paralysis even if inoculated in the spinal cord with F113 in a dosage of $10^6$ TCID$_{50}$.

The foregoing indicates that the sensitivity attained by inoculation of F113 into the spinal cord of Tg1 is 10,000-fold or more higher than that by inoculation into the brain. The same level of sensitivity was obtained whether Tg1 used was male or female.

The PD$_{50}$ of the F113 strain in Tg1 was calculated on the basis of the results in FIG. 4. The PD$_{50}$ indicated that a paralysis occurred even in a low dosage of $10^{1.6}$ TCID$_{50}$, and significantly high sensitivity was thus found.

With respect to Tg21, the inoculation of F113 into the spinal cord caused a paralysis in 4 out of 14 animals (28.6%) even in a low dosage of $10_3$ TCID$_{50}$ (FIG. 4).

From the foregoing, it was found that the inoculation of the virus into the spinal cord of TgPVR was effective for examination of neurovirulence.

Comparative Example 1.

Neurovirulence Test Using Monkey

The neurovirulence test using monkeys was conducted in the WHO method.

The above 7 viruses used in the TgPVR test were also used in this test. 12 cynomolgus monkeys were used for each virus by inoculating 0.1 ml sample ($10^6$ TCID$_{50}$) into the spinal cord except that 5 monkeys were used for S1D-38/2 and S1D-38/4, respectively. Pathological examination was made of tissues from the central nervous system on the 19th day after inoculation.

To determine the lesion score in the pathological examination of central nervous system, grade 1 was given where mononuclear cells have grown and are infiltrated, and grade 2 or more was given where further denaturation has occurred in nerve cells. In this case, grade 2 was given where cell infiltration involves minimal denaturation of nerve cells; grade 3 was given where cell infiltration involves extensive denaturation of nerve cells; and grade 4 was given where nerve cells have been massive denatured and have disappeared. Lesions in 7 sites in the brain (cortex, midbrain, thalamus, pons, cerebellum, upper and lower medulla oblongata), 12 sites in the cervical cord, and 18 sites in the lumbar cord were examined respectively on the left and right sides, and the results were recorded. The average of the pathological changes in the brain, the cervical cord and the lumbar cord was determined for each monkey, and then the average in a group of animals was determined as lesion score (LS).

Table 2 shows a comparison between the results of the neurovirulence test using monkeys (in terms of LS) and those of the neurovirulence test using Tg21 as TgPVR (in terms of PD$_{50}$) with respect to 7 viruses including F113 derived from type 1 of Sabin strain.

TABLE 2

| neurovirulence test | | virus strain | | | | | | |
|---|---|---|---|---|---|---|---|---|
| | | F113 | S1A | S1B | S1C | S1D | S1D-38/2 | S1D 38/2 |
| monkey | LS | 0.83 | 0.85 | 0.33 | 0.79 | 0.77 | 1.32 | 2.07 |
| TgPVR21 | $PD_{50}$ ($TCID_{50}$) | $10^{3.3}$ | $10^{3.4}$ | $10^{4.3}$ | $10^{3.7}$ | $10^{3.6}$ | $10^{2.9}$ | $10^{2.4}$ |

As shown in Table 2, the LS values range from 0.77 to 0.85 where 4 viruses (F113, S1A, S1C and S1D) were examined in monkeys. The $PD_{50}$ values range from $10^{3.7}$ to $10^{3.3}$ $TCID_{50}$ where the same viruses were examined in TgPVR.

When S1B was examined, the LS value was 0.33 and the $PD_{50}$ value was $10^{4.3}$ $TCID_{50}$, indicating that this virus is extremely attenuated as compared with other viruses.

When S1D-38/2 and S1D-38/4 were examined, the LS values were 1.32 and 2.07, respectively, and the $PD_{50}$ values were $10^{2.9}$ $TCID_{50}$ and $10^{2.4}$ $TCID_{50}$, respectively.

From these results, it was found that clinical phenomena in terms of both $PD_{50}$ and $LD_{50}$ are correlated well with each other and can thus be satisfactory indicators of neurovirulence in the test system using TgPVR, while lesion score (LS) of central nervous system is the only indicator of neurovirulence in the test system using monkeys.

Figure 6:
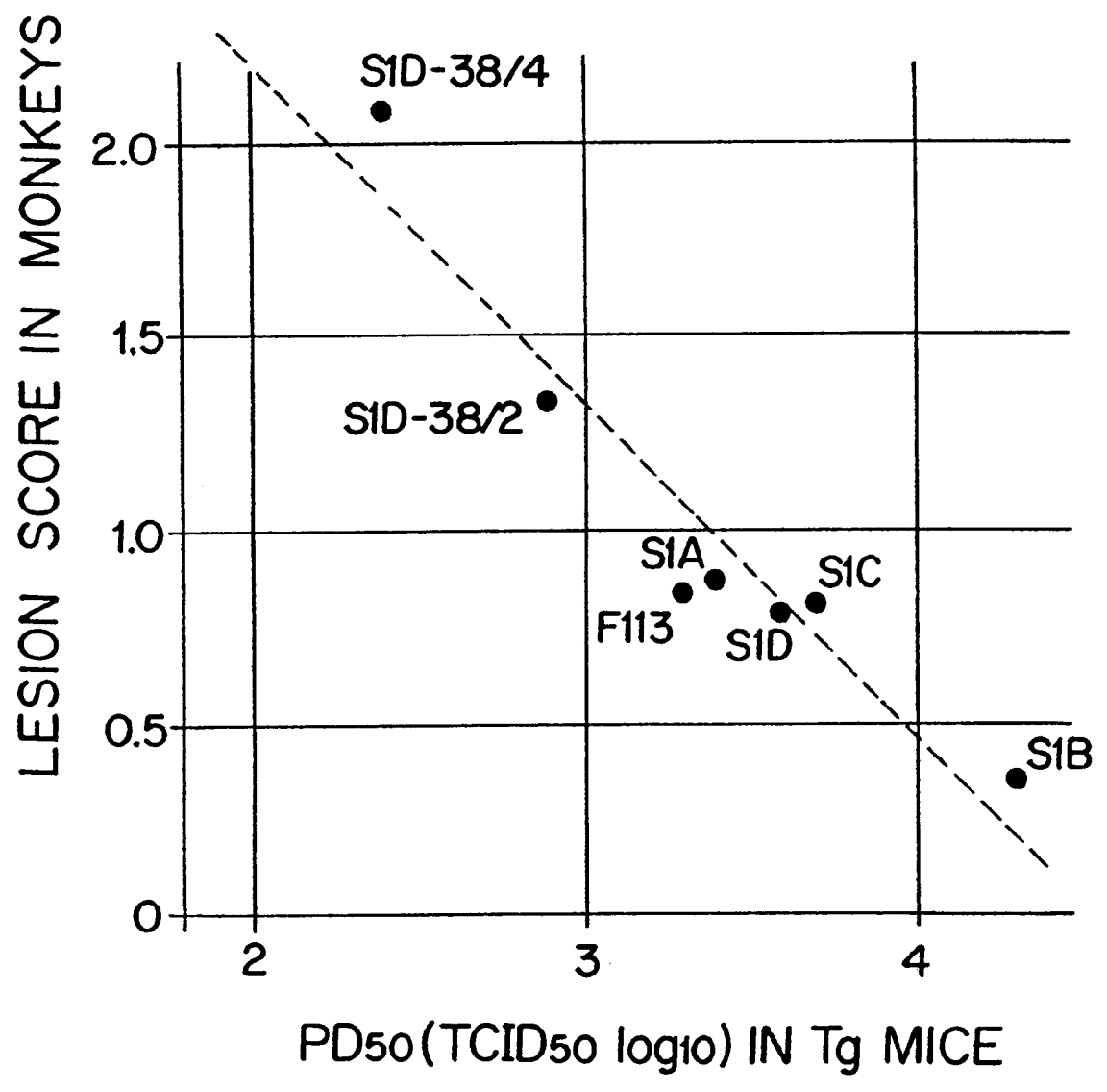

FIG. 6 shows a correlation between the above LS in monkeys and $PD_{50}$ in TgPVR21 values. There is a very good correlation therebetween with a coefficient of correlation ($\gamma$) of −0.96.

These results indicate that the TgPVR animals attained the same level of sensitivity as that of monkeys, even for type 1 of Sabin strain as a group of viruses with different levels of neurovirulence, and they can be used in an assay system of neurovirulence for polio vaccine. Reference Example 1. Distribution of the virus in the central nervous system after inoculation intraspinally F113 was inoculated into the spinal cord of Tg21 in a dosage of $10^4$ $TCID_{50}$, and then the virus was recovered from the brain, spinal cord and blood in order to determine where the virus was multiplied and distributed in the central nervous system and blood.

The distribution of the virus in the central nervous system was examined for 3 days after inoculation in the following manner.

F113 was inoculated into the spiral cord of Tg21 (9 animals per group) in a dosage of $10^4$ $TCID_{50}$, i.e. an amount causing paralysis in nearly 100% of Tg21 animals. After 1, 2 and 3 days, the brain, spiral cord and blood were collected respectively from 2 animals from group. The amount of virus was measured therefrom in the following manner. 9 parts of medium (Medium 199) was added to 1 part of the above brain or spinal cord. The mixture was homogenized under cooling in a homogenizer and centrifuged at 2000 r.p.m. for 20 minutes. The supernatant was filtered through a filter with 0.45 μm pores. The virus content in the filtrates were measured by roller tube method in GMK2 described above. The virus in blood was determined after addition of heparin to the blood collected above.

Figure 7:
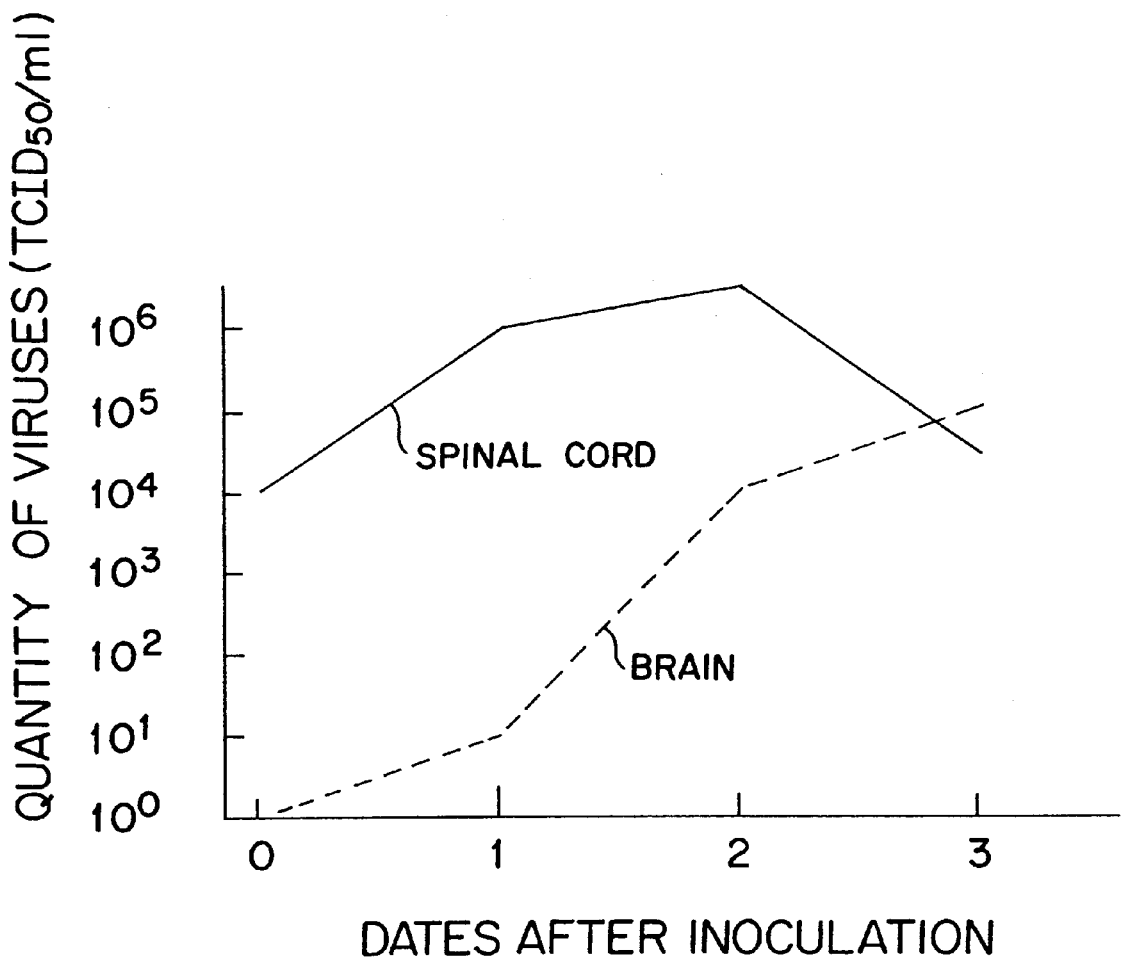

The results are shown in FIG. 7.

As shown in this graph, F113 started to multiply in the spinal cord soon after inoculation, and the number of viruses reached the maximum 2 days later. In the brain, the virus was observed to multiply 2 or 3 days after inoculation. No virus could be recovered from the blood.

Conventional non-transgenic ICR mice were also examined as described above. The results indicated that the virus was not multiplied in the brain, spinal cord or blood.

INDUSTRIAL APPLICABILITY

According to the present invention there can be provided a very sensitive method for examining-the neurovirulence of attenuated polio vaccine in simple procedures. The results of the present method using TgPVR correlate well with those of the conventional neurovirulence test using monkeys. The present invention further provides the following advantages: a large number of almost homogenous and zoonosis-free animals can be handled relatively easily; results on neurovirulence test of polio vaccine are stable and reliable; and the polio virus including virulent to attenuated strains can be subjected to examination of neurovirulence.

Hence, many consistency tests, particularly neurovirulence tests of polio vaccine virus can be carried out using non-primate animals to produce, safe and effective polio vaccines.

What is claimed is:

1. A method for examining the neurovirulence of a polio vaccine, which comprises:
    (a) inoculating an amount of the polio vaccine into the spinal cord of a transgenic mouse whose genome comprises a transgene encoding a human polio virus receptor such that said receptor is expressed on the cells of the mouse, wherein said polio vaccine comprises a polio virus, and wherein said inoculation comprises using a microsyringe having a two-step needle comprising a proximate barrel and a distal barrel having a smaller diameter than the diameter of the proximate barrel; and
    (b) observing the transgenic mouse for clinical symptoms of polio virus infection, and/or examining the transgenic mouse for pathological changes in its central nervous system.

2. The method according to claim 1, wherein the polio virus is an attenuated strain of type 1, 2 or 3 of polio virus.

3. The method of claim 1, wherein the two-step needle has a 33-gauge distal barrel.

4. The method of claim 1, wherein the two-step needle has a distal barrel that is about 7 mm in length.

* * * * *

UNITED STATES PATENT AND TRADEMARK OFFICE
CERTIFICATE OF CORRECTION

PATENT NO.    : 5,986,171

DATED         : November 16, 1999

INVENTOR(S)   : Abe et al.

It is certified that error appears in the above-identified patent and that said Letters Patent is hereby corrected as shown below:

On the title page at [75] Inventors: correct the spelling of "So Hashizume" to --Sou Hashizume--.

On the title page at [86] PCT No.: PCT/JP94/00451, in the second to last line and the last line: change "Nov. 5, 1995" to --Nov. 15, 1995--.

Signed and Sealed this

Third Day of April, 2001

*Attest:*

NICHOLAS P. GODICI

*Attesting Officer*    Acting Director of the United States Patent and Trademark Office